United States Patent [19]
Müller et al.

[11] 3,949,083
[45] Apr. 6, 1976

[54] PYRAZOL-5-ONES

[75] Inventors: Eike Müller; Karl Meng, both of Wuppertal; Egbert Wehinger, Neviges; Harald Horstmann, Wuppertal, all of Germany

[73] Assignee: Bayer Aktiengesellschaft, Germany

[22] Filed: Apr. 9, 1974

[21] Appl. No.: 459,407

[30] Foreign Application Priority Data
Apr. 17, 1973 Germany............................ 2319281

[52] U.S. Cl. ............................................... 424/273
[51] Int. Cl.[2] ........................................ A61K 31/415
[58] Field of Search ..................................... 424/273

[56] References Cited
UNITED STATES PATENTS
3,190,888  6/1965  Wolf et al. ........................... 260/310
FOREIGN PATENTS OR APPLICATIONS
2,068,413  8/1971  France................................. 424/273
961,037  6/1964  United Kingdom................. 424/273

*Primary Examiner*—Donald B. Moyer

[57] ABSTRACT

Pharmaceutical compositions useful for effecting diuresis and saluresis and for treating hypertension in humans and animals are produced by combining a pyrazol-5-one of the formula:

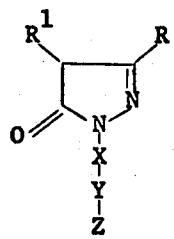

or a pharmaceutically acceptable nontoxic salt thereof wherein
R is hydrogen, lower alkyl or amino;
$R^1$ is lower alkyl, alkenyl of 2 to 4 carbon atoms, monoaryl or monoaralkyl unsubstituted or substituted in the aryl moiety by 1 or 2 of the same or different substituents selected from the group consisting of lower alkyl, lower alkenyl, lower alkoxy, lower alkenoxy, halogen, nitro, cyano and trifluoromethyl;
X is methylene, ethylene, methylene wherein 1 hydrogen atom is substituted by lower alkyl, or ethylene wherein 1 hydrogen atom is substituted by lower alkyl or 1 hydrogen atom on each of the two carbon atoms is substituted by lower alkyl;
Y is a direct bond, oxygen or sulphur, provided that when X is methylene, Y is a direct bond; and
Z is aryl unsubstituted or nuclear substituted by:
  a. 3 halogens;
  b. 1 or 2 of the same or different substituents selected from the group consisting of halogen, trifluoromethyl, lower alkyl, lower alkenyl, lower alkoxy, lower alkenoxy, cycloalkyl of 5 to 7 carbon atoms and cycloalkenyl of 5 to 7 carbon atoms;
  c. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, or $-SO_n-$lower alkyl wherein n is 0, 1 or 2;
  d. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, or $-SO_n-$lower alkyl wherein n is 0, 1 or 2, and 1 or 2 of the same or different substituents selected from the group consisting of lower alkyl, lower alkenyl, lower alkoxy, halogen, and trifluoromethyl;
  e. dilower alkylamino, carbamoyl, lower alkylcarbamoyl, dilower alkylcarbamoyl, sulphamyl, lower alkylsulphamyl, or dilower alkylsulphamyl wherein the nitrogen atom is a member of 5-, 6- or 7-membered heterocyclic ring or said ring which contains oxygen as an additional ring member; or
  f. a fused, saturated or unsaturated 5-, 6- or 7-membered ring or said ring which additionally contains 1 or 2 oxygen atoms or 1 sulphur atom, with a pharmaceutically acceptable nontoxic inert diluent or carrier.

The compositions are preferably administered orally or parenterally and in the latter case, sterile or isotonic aqueous solutions are preferred.

28 Claims, No Drawings

PYRAZOL-5-ONES

The present invention relates to pharmaceutical compositions which are useful for effecting diuresis and saluresis in humans and animals and for treating hypertension in humans and animals. These compositions are characterized by the use of pyrazol-5-ones or pharmaceutically acceptable non-toxic salts thereof as the active agent.

3-Aminopyrazolones have been used as color couplers for color photography (A. Weissberger et al. J. Amer. Chem. Soc. 64, 2133 (1942), and as intermediates for the preparation of color couplers (British Pat. No. 599,919; U.S. Pat. No. 2,367,523; U.S. Pat. No. 2,376,380; U.S. Pat. No. 2,511,231; U.S. Pat. No. 2,600,788; U.S. Pat. No. 2,619,419; U.S. Pat. No. 2,672,417).

Pyrazol-5-one derivatives are used as antipyretics, analgesics and antiphlogistics (cf. G. Ehrhart and H. Ruschig, "Arzneimittel", Vol. 1, P. 148 (1972)).

However, no diuretic, saluretic or antihypertensive activity is known for pyrazol-5-one derivatives.

It has now been discovered that pharmaceutical compositions can be prepared for use as diuretics, saluretics and antihypertensives by combining a pyrazol-5-one or pharmaceutically acceptable nontoxic salt thereof as hereinafter defined with a pharmaceutically acceptable nontoxic inert diluent or carrier.

The present invention also comprises administering to humans or animals in need of diuretic, saluretic or antihypertensive therapy, pyrazol-5-ones or pharmaceuticallly acceptable nontoxic salts thereof as hereinafter defined.

More particularly, the present invention comprises a pharmaceutical composition which comprises a diuretic, saluretic or antihypertensive amount of a pyrazol-5-one of the formula:

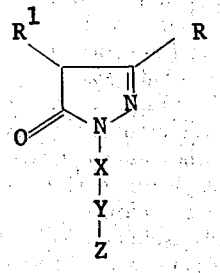

or a pharmaceutically acceptable nontoxic salt thereof wherein

R is hydrogen, alkyl especially lower alkyl, or amino;
$R^1$ is alkyl especially lower alkyl, lower alkenyl, aryl especially monoaryl, aralkyl especially monoaralkyl unsubstituted or substituted in the ring by 1 or 2 of the same or different substituents selected from the group consisting of alkyl especially of 1 to 4 carbon atoms, alkenyl especially of 2 to 4 carbon atoms, alkoxy especially of 1 to 4 carbon atoms, alkenoxy especially of 2 to 4 carbon atoms, halogen, nitro, cyano, and triflouromethyl;
X is methylene, ethylene, methylene wherein 1 hydrogen atom is substituted by lower alkyl, or ethylene wherein 1 hydrogen atom is substituted by lower alkyl or 1 hydrogen atom on each of the two carbon atoms is substituted by lower alkyl;
Y is a direct bond, oxygen or sulphur, provided that when X is methylene, Y is a direct bond; and Z is aryl especially phenyl or naphthyl unsubstituted or substituted in the ring by:
a. 3 halogen atoms;
b. 1 or 2 of the same or different substituents selected from the group consisting of halogen, trifluoromethyl, alkyl especially of 1 to 4 carbon atoms, alkenyl especially of 2 to 4 carbon atoms, alkoxy especially of 1 to 4 carbon atoms, alkenoxy especially of 2 to 4 carbon atoms, cycloalkyl of 5, 6 or 7 carbon atoms, and cycloalkenyl of 5, 6 or 7 carbon atoms;
c. lower alkylamino, dilower alkylamino, trifluoromethoxy, nitro, cyano, arbamoyl, lower alkylcarbamoyl, dilower alkylcarbamoyl, sulphamyl, lower alkylsulphamyl, dilower alkylsulphamyl, or $-SO_n$-lower alkyl wherein $n$ is 0, 1 or 2;
d. lower alkylamino, dilower alkylamino, trifluoromethoxy, nitro, cyano, carbamoyl, lower alkylcarbamoyl, dilower alkylcarbamoyl, sulphamyl, lower alkylsulphamyl, dilower alkylsulphamyl, or $-SO_n$-lower alkyl wherein $n$ is 0, 1 or 2, and 1 or 2 of the same or different substituents selected from the group consisting of lower alkyl, lower alkenyl, lower alkoxy, halogen, and trifluoromethyl;
e. dilower alkylamino, carbamoyl, lower alkylcarbamoyl, dilower alkylcarbamoyl, sulphamyl, lower alkylsulphamyl, or dilower alkylsulphamyl wherein the nitrogen atom is a member of a 5-, 6- or 7-membered heterocyclic ring or said ring which contains oxygen as an additional ring member; or
f. a fused, saturated or unsaturated 5-, or 6- or 7membered ring or said ring which additionally contains 1 or 2 oxygen atoms or 1 sulphur atom,
in combination with a pharmaceutically acceptable nontoxic inert diluent or carrier.

As used herein the expression "compounds of the present invention" means both the pyrazol-5-ones of formula I above and their pharmaceutically acceptable nontoxic salts.

The phrase "lower alkyl", "lower alkenyl", "lower alkoxy" and "lower alkenoxy" include both straight and branched chain moieties.

The compounds according to the present invention exist not only in the form shown in formula I but also in the following tautomeric forms:

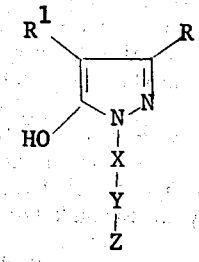
(a)

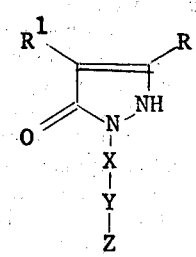
(b)

Specifically, the 3-aminopyrazol-5-ones may, additionally, occur in the forms I (c) and I (d):

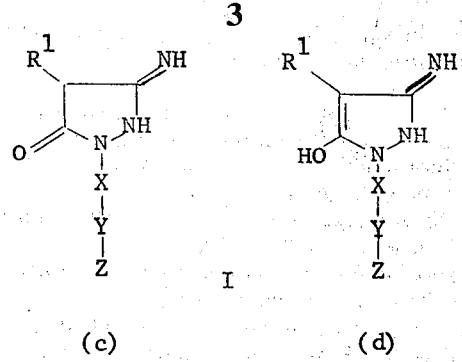

(c)    (d)

The present invention includes the use of the pyrazol-5-ones and their pharmaceutically acceptable nontoxic salts in any of the tautomeric forms in which they exist.

In addition, when X in formula I contains an asymmetric carbon atom, the compound exists as a racemate and can be resolved into its antipodes. The compositions of the present invention must include the pyrazol-5-ones and pharmaceutically acceptable nontoxic salts thereof in the form of the optical isomers as well as the racemates.

According to one embodiment of the present invention:

R is hydrogen, alkyl of 1 to 4 carbon atoms, or amino;
$R^1$ is alkyl of 1 to 4 carbon atoms, alkenyl of 2 to 4 carbon atoms, phenyl, benzyl, or phenyl or benzyl substituted in the nuclear portion by 1 or 2 of the same or different substitutents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen, nitro, cyano and trifluoromethyl;
X is methylene, ethylene, methylene wherein 1 hydrogen atom is substituted by alkyl of 1 to 4 carbon atoms or ethylene wherein 1 hydrogen atom is substituted by alkyl of 1 to 4 carbon atoms or 1 hydrogen atom on each of the two carbon atoms is substituted by alkyl of 1 to 4 carbon atoms; and
Z is phenyl or naphthyl unsubstituted or nuclear substituted by:
  a. 3 halogens;
  b. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, alkenoxy of 2 to 4 carbon atoms, cycloalkyl of 5 to 7 carbon atoms, and cycloalkenyl of 5 to 7 carbon atoms;
  c. alkylamino of 1 to 4 carbon atoms in the alkyl moiety, dialkylamino of 1 to 4 carbon atoms in each alkyl moiety, trifluoromethoxy, nitro, cyano, carbamoyl, alkylcarbamoyl of 1 to 4 carbon atoms in the alkyl moiety, dialkylcarbamoyl or 1 to 4 carbon atoms in the alkyl moiety, sulphamyl, alkylsulphamyl of 1 to 4 carbon atoms in the alkyl moiety, dialkylsulphamyl of 1 to 4 carbon atoms in each alkyl moiety, or -$SO_n$-alkyl of 1 to 4 carbon atoms wherein $n$ is 0, 1 or 2;
  d. alkylamino of 1 to 4 carbon atoms in the alkyl moiety, dialkylamino of 1 to 4 carbon atoms in each alkyl moiety, trifluoromethoxy, nitro, cyano, carbamoyl, alkylcarbamoyl of 1 to 4 carbon atoms in the alkyl moiety, dialkylcarbamoyl of 1 to 4 carbon atoms in the alkyl moiety, sulphamyl, alkylsulphamyl of 1 to 4 carbon atoms in the alkyl moiety, dialkylsulphamyl of 1 to 4 carbon atoms in each alkyl moiety, or -$SO_n$-alkyl of 1 to 4 carbon atoms wherein $n$ is 0, 1 or 2, and 1 or 2 of the same or different substituents selected from the group consisting of alkyl of 1 to 4 carbon atoms, alkenyl of 2 to 4 carbon atoms, alkoxy of 1 to 4 carbon atoms, halogen and trifluoromethyl;
  e. dialkylamino of 1 to 4 carbon atoms in each alkyl moiety, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms, or dialkylsulphamyl of 1 to 4 carbon atoms in each alkyl moiety wherein the nitrogen atom is a member of a 5-, 6- or 7-membered heterocyclic ring or said ring which contains oxygen as an additional ring member; or
  f. a fused, saturated or unsaturated 5-, 6- or 7-membered ring or said ring which additionally contains 1 or 2 oxygen atoms or 1 sulphur atom.

According to another embodiment of the present invention:

R is hydrogen, alkyl of 1 to 4 carbon atoms, or amino;
$R^1$ is alkyl of 1 to 4 carbon atoms, phenyl, benzyl, or benzyl having 1 or 2 nuclear substituents which are the same or different selected from the group consisting of alkyl of 1 to 4 carbon atoms, alkenyl of 2 to 4 carbon atoms, alkoxy of 1 to 4 carbon atoms, alkenoxy of 2 to 4 carbon atoms, fluorine, chlorine, bromine, nitro, cyano, and trifluoromethyl;
X is methylene, ethylene, or methylene or ethylene wherein 1 hydrogen atom of each carbon atom is substituted by alkyl of 1 to 4 carbon atoms; and
Z is phenyl or naphthyl unsubstituted or substituted by:
  a. 1 or 2 alkyl moieties of 1 to 8 carbon atoms or alkenyl moieties of 2 to 8 carbon atoms;
  b. 1 or 2 alkoxy moieties of 1 to 6 carbon atoms, alkenoxy moieties of 2 to 6 carbon atoms, cycloalkyl moieties of 5, 6 or 7 carbon atoms, or cycloalkenyl moieties of 5, 6 or 7 carbon atoms;
  c. 1, 2 or 3 halogens;
  d. 1 or 2 trifluoromethyl moieties;
  e. trifluoromethoxy, nitro, cyano, dialkylamino of 1 to 4 carbon atoms in each alkyl moiety, carbamoyl, alkylcarbamoyl of 1 to 4 carbon atoms, dialkylcarbamoyl of 1 to 4 carbon atoms, sulphamyl, alkylsulphamyl of 1 to 4 carbon atoms, or dialkylsulphamyl of 1 to 4 carbon atoms, or said dialkylamino, carbamoyl, alkylcarbamoyl, dialkylcarbamoyl, sulphamyl, alkylsulphamyl, or dialkylsulphamyl wherein the nitrogen atom is a member of a 5-, or 6- or 7-membered heterocyclic ring or said ring which contains oxygen as an additional ring member;
  f. -$SO_n$-alkyl of 1 to 4 carbon atoms wherein $n$ is 0, 1 or 2; or
  g. a fused, saturated or unsaturated 5-, or 6- or 7-membered ring or said ring which additionally contains 1 or 2 oxygen atoms or 1 sulphur atom as ring members.

According to another embodiment of the present invention: Z is phenyl, naphthyl, or phenyl substituted by:
  a. 1 or 2 alkyl moieties of 1 to 4 carbon atoms or alkenyl moieties of 2 to 4 carbon atoms;
  b. 1 or 2 alkoxy moieties of 1 to 6 carbon atoms, alkenoxy moieties of 2 to 6 carbon atoms, cycloalkyl moieties of 5 to 7 carbon atoms, or cycloalkenyl moieties of 5 to 7 carbon atoms;
c. 1, 2 or 3 halogens;
d. 1 or 2 trifluoromethyl moieties;
e. trifluoromethoxy, nitro, cyano, dialkylamino of 1 to 4 carbon atoms, carbamoyl, alkylcarbamoyl of 1 to 4 carbon atoms, dialkylcarbamoyl of 1 to 4 carbon atoms, sulphamyl, alkylsulphamyl of 1 to 4 carbon atoms, or dialkylsulphamyl of 1 to 4 carbon atoms; or
f. $-SO_n-$alkyl of 1 to 4 carbon atoms wherein n is 0 or 2.

According to another embodiment of the present invention:
R is hydrogen, alkyl of 1 or 2 carbon atoms, or amino;
$R^1$ is alkyl of 1 to 2 carbon atoms;
X is methylene, ethylene, methylene substituted by alkyl of 1 to 3 carbon atoms, ethylene substituted by methyl, or ethylene wherein 1 hydrogen atom or each of the two carbon atoms is substituted by methyl;
Y is a direct bond or oxygen; and
Z is phenyl, naphthyl, or phenyl substituted by 1 or 2 of the same or different substituents selected from the group consisting of chlorine, bromine, fluorine, iodine, alkyl of 1 to 4 carbon atoms, trifluoromethyl, trifluoromethoxy, cyano, nitro, sulphamyl, alkoxy of 1 to 4 carbon atoms, and alkylamino of 1 or 2 carbon atoms, or 1 substituent selected from the group consisting of phenyl, cyclohexyl and a trimethylene or tetramethylene moiety which forms a 5- or 6-membered ring together with two carbon atoms of the phenyl ring.

According to another embodiment of the present invention:
R is hydrogen, methyl or amino;
$R^1$ is methyl;
X is methylene, ethylene, methylene substituted by methyl or propyl, ethylene substituted by methyl or ethylene wherein 1 hydrogen atom of each of the two carbon atoms is substituted by a methyl moiety;
Y is a direct bond or oxygen;
Z is phenyl, naphthyl, or phenyl substituted by chlorine, bromine, fluorine, iodine, methyl, isopropyl, n-butyl, trifluoromethyl, cyano, nitro, phenyl, cyclohexyl, sulphamyl, isopropoxy, trifluoromethoxy, dimethylamino, trimethylene, tetramethylene, dichloro, dibromo, chloro and bromo, fluoro and chloro, chloro and methyl, fluoro and trifluoromethyl, methyl and trifluoromethyl, or sulphamyl and chloro.

According to another embodiment of the present invention:
R is hydrogen, amino or alkyl of 1 or 2 carbon atoms;
$R^1$ is alkyl of 1 to 4 carbon atoms, allyl, phenyl or benzyl unsubstituted or substituted in the ring by alkoxy of 1 or 2 carbon atoms;
X is methylene, ethylene, methylene substituted by alkyl of 1 to 3 carbon atoms, or ethylene substituted by methyl;
Y is a direct bond, oxygen or sulphur provided that when X is methylene, Y is a direct bond; and
Z is phenyl, naphthyl, or phenyl substituted by 1 or 2 of the same or different substituents selected from the group consisting of chlorine, fluorine, alkyl of 1 to 4 carbon atoms, and trifluoromethyl.

According to another embodiment of the present invention:
R is hydrogen, amino or methyl;
$R^1$ is alkyl of 1 to 4 carbon atoms, allyl, phenyl, benzyl or methoxybenzyl;
X is methylene, ethylene, methylene substituted by alkyl of 1 to 3 carbon atoms, or ethylene substituted by methyl;
Y is a direct bond, oxygen or sulphur provided that when X is methylene, Y is a direct bond; and
Z is phenyl, naphthyl, or phenyl substituted by fluorine, chlorine, alkyl of 1 to 3 carbon atoms, two chlorines, or methyl and trifluoromethyl.

The pyrazol-5-ones of the present invention may be prepared by reacting a hydrazine of the formula II:

$$Z-Y-X-NH-NH_2 \qquad \text{II}$$

wherein
X, Y and Z are as above defined,
with an acetic acid derivative of the formula III:

$$Y^1-\underset{\underset{Y^2}{|}}{\overset{\overset{R^1}{|}}{C}}-C\overset{\displaystyle \nearrow O}{\underset{\displaystyle \searrow X^1}{}} \qquad \text{III}$$

wherein
$X^1$ is hydroxy, lower alkoxy, aralkoxy preferably comprising a monoaryl moiety and a lower alkoxy moiety, amino or lower alkylamino;
$R^1$ is as above defined; and either
$Y^1$ is hydrogen and
$Y^2$ is cyano or a moiety of the formula:

$$-C\overset{\displaystyle \nearrow O}{\underset{\displaystyle \searrow Y^3}{}}$$

wherein
$Y^3$ is hydrogen or straight or branched chain alkyl of 1 to 4 carbon atoms; or
$Y^1$ and $Y^2$ together form the moiety:

$$=C\overset{\displaystyle \nearrow NH_2}{\underset{\displaystyle \searrow Y^4}{}}$$

wherein
$Y^4$ is lower alkoxy, aryloxy preferably monoaryloxy, aralkoxy preferably comprising a monoaryl moiety and a lower alkoxy moiety, lower alkylmercapto, aralkylmercapto preferably comprising a monoaryl moiety in the lower alkyl moiety, or amino,
either in the presence or the absence of an inert solvent and of a basic or acetic catalyst such as an alkali metal hydroxide, carbonate, halogen hydracid, sulphuric acid or a sulphonic acid, art a temperature between 10°C and 200°C.

The pyrazol-5-ones of formula I and their pharmaceutically acceptable nontoxic salts may be interconverted according to techniques which are per se known in the art.

The racemates according to the present invention may be resolved into their optical antipodes:
1. According to methods known in the literature (see, e.g. Houben Weyl's "Methoden der Organischen Chemie" IV/2, page 509 ff) by interaction of a racemic compound used according to the invention with a chiral medium, preferably by reaction of the said compound with a derivative of an optically active acid (e.g. camphorsulphonic acid, bromo-camphorsulphonic acid or quinic acid) or of an optically active base (e.g. brucine, morphine or strychnine) to give a mixture of diastereoisomeric reaction products. These products can, with the aid of physicochemical methods (e.g. fractionation) be separated and prepared pure, and subsequently again resolved into their components or 2. By reaction of the optically pure hydrazine of the formula II (which can be prepared by methods known from the literature) with an acetic acid derivative of the formula III, e.g.

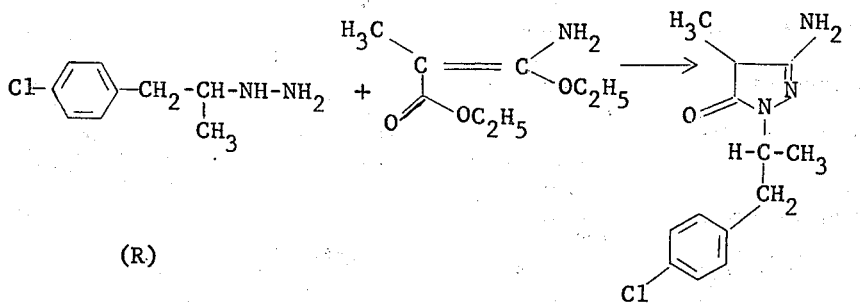

(R.)  (R)

The following compounds are representative of those of the present invention:

3-amino-4-methyl-1-(3-chlorobenzyl)-pyrazol-5-one
3-amino-4-methyl-1-(3-bromobenzyl)-pyrazol-5-one
3-amino-4-methyl-1-(4-bromobenzyl)-pyrazol-5-one
3-amino-4-methyl-1-(3-fluorobenzyl)-pyrazol-5-one
3-amino-4-methyl-1-(4-fluorobenzyl)-pyrazol-5-one
3-amino-4-methyl-1-(4-iodobenzyl)-pyrazol-5-one
3-amino-4-methyl-1-(4-chloro-3-bromobenzyl)-pyrazol-5-one
3-amino-4-methyl-1-(4-bromo-3-chlorobenzyl)-pyrazol-5-one
3-amino-4-methyl-1-(4-fluoro-3-chlorobenzyl)-pyrazol-5-one
3-amino-4-methyl-1-(3,4-dibromobenzyl)-pyrazol-5-one
3-amino-4-methyl-1-(4-methylbenzyl)-pyrazol-5-one
3-amino-4-methyl-1-(4 -isopropylbenzyl)-pyrazol-5-one
3-amino-4-methyl-1-(4-n-butylbenzyl)-pyrazol-5-one
3-amino-4-methyl-1-(4-phenylbenzyl)-pyrazol-5-one
3-amino-4-methyl-1-(4-cyclohexylbenzyl)-pyrazol-5-one
3-amino-4-methyl-1-(4-trifluoromethylbenzyl)-pyrazol-5-one
3-amino-4-methyl-1-(4-methyl-3-chlorobenzyl)-pyrazol-5-one
3-amino-4-methyl-1-(3-methyl-4-chlorobenzyl)-pyrazol-5-one
3-amino-4-methyl-1-(4-trifluoromethyl-3-chlorobenzyl)-pyrazol-5-one
3-amino-4-methyl-1-(4-methyl-3-trifluoromethylbenzyl)-pyrazol-5-one
3-amino-4-methyl-1-(4-chloro-3-trifluoromethylbenzyl)-pyrazol-5-one
3-amino-4-methyl-1-(4-cyanobenzyl)-pyrazol-5-one
3-amino-4-methyl-1-(4-nitrobenzyl)-pyrazol-5-one
3-amino-4-methyl-1-(4-sulphonamidobenzyl)-pyrazol-5-one
3-amino-4-methyl-1-(4-sulphonamido-3-chlorobenzyl)-pyrazol-5-one
3-amino-4-methyl-1-(4-methoxbenzyl)-pyrazol-5-one
3-amino-4-methyl-1-(4-isopropoxybenzyl)-pyrazol-5-one
3-amino-4-methyl-1-(4-trifluoromethoxbenzyl)-pyrazol-5-one
3-amino-4-methyl-1-(4-dimethylaminobenzyl)-pyrazol-5-one
3-amino-4-methyl-1-(3,4-trimethylenebenzyl)-pyrazol-5-one
3-amino-4-methyl-1-(3,4-tetramethylenebenzyl)-pyrazol-5-one
3,4-dimethyl-1-(4-chlorobenzyl)-pyrazol-5-one
3,4-dimethyl-1-(4-bromobenzyl)-pyrazol-5-one
3,4-dimethyl-1-(3,4-dichlorobenzyl)-pyrazol-5-one
3,4-dimethyl-1-(4-bromo-3-chlorobenzyl)-pyrazol-5-one
3,4-dimethyl-1-(4-chloro-3-bromobenzyl)-pyrazol-5-one
3,4-dimethyl-1-(4-methylbenzyl)-pyrazol-5-one
3,4-dimethyl-1-(4-trifluoromethylbenzyl)-pyrazol-5-one
3,4-dimethyl-1-(4-methyl-3-chlorobenzyl)-pyrazol-5-one
3,4-dimethyl-1-(3-methyl-4-chlorobenzyl)-pyrazol-5-one
3,4-dimethyl-1-(4-trifluoromethyl-3-chlorobenzyl)-pyrazol-5-one
3,4-dimethyl-1-(4-methyl-3-trifluoromethylbenzyl)-pyrazol-5-one
3,4-dimethyl-1-(4-chloro-3-trifluoromethylbenzyl)-pyrazol-5-one
3,4-dimethyl-1-(naphthyl-(2)-methyl)-pyrazol-5-one
4-methyl-1-(4-chlorobenzyl)-pyrazol-5-one
4-methyl-1-(4-methyl-3-chlorobenzyl)-pyrazol-5-one
3-amino-4-methyl-1-(α-methyl-3-chlorobenzyl)-pyrazol-5-one
3-amino-4-methyl-1-(α-methyl-3,4-dichlorobenzyl)-pyrazol-5-one
3-amino-4-methyl-1-(α-methyl-3-chloro-4-methylbenzyl)-pyrazol-5-one
3-amino-4-methyl-1-(α-methyl-4-trifluoromethylbenzyl)-pyrazol-5-one 3-amino-4-methyl-1-(α-methyl-3-chloro-4-bromobenzyl)-pyrazol-5-one
3-amino-4-methyl-1-(α-(naphthyl-(2))-ethyl)-pyrazol-5-one
3,4-dimethyl-1-(α-methyl-4-4-chlorobenzyl)-pyrazol-5-one
3,4-dimethyl-1-(α-methyl-3-3-chloro-4-methylbenzyl)-pyrazol-5-one
3,4-dimethyl-1-(α-methyl-4-bromo-3-chlorobenzyl)-pyrazol-5-one
3,4-dimethyl-1-(α-methyl-4-trifluoromethylbenzyl)-pyrazol-5-one
3,4-dimethyl-1-(α-(naphthyl-(2))-ethyl)-pyrazol-5-one
3-amino-4-methyl-1-(α-benzyl-n-propyl)-pyrazol-5-one
3-amino-4-methyl-1-(α,β-dimethyl-β-phenylethyl)-pyrazol-5-one
3-amino-4-methyl-1-(β-methyl-β-phenoxyethyl)-pyrazol-5-one
3-amino-4-methyl-1-(β-(naphthyl-(2)-oxy)-ethyl)-pyrazol-5-one
3,4-dimethyl-1-(α-benzyl-n-propyl)-pyrazol-5-one
3,4-dimethyl-1-(α,β-dimethyl-β-phenylethyl)-pyrazol-5-one
3,4-dimethyl-1-(β-methyl-β-phenoxyethyl)-pyrazol-5-one
3,4-dimethyl-1-(β-(naphthyl-(2)-oxy)-ethyl)-pyrazol-5-one The pharmaceutical compositions of the present invention contain a major or minor amount e.g. 99.5 to 0.1%, preferably 90 to 0.5% of at least one pyrazol-5-one as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the parenteral dosage will be from 0.01 to 50 mg/kg, preferably 0.1 to 10 mg/kg, of body weight per day, and the oral dosage will be from 0.1 to 500 mg/kg, preferably 0.5 to 100 mg/kg, of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through the screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

The preferred daily dose for parenteral administration is 0.5 mg to 5 g., especially 5 mg to 1 g., and for oral administration the preferred daily dose is 5 mg to 50 g., especially 25 mg to 10 g. of active ingredient.

While the routes of administration include oral, parenteral (i.e. intramuscular, intraperitoneal, and intravenous) and rectal, oral and parenteral are particularly preferred. For parenteral administration, it is preferred that the solutions and emulsions be sterile and, if appropriate, blood-isotonic.

Examples of oral and parenteral administrable compositions include the following:

a. Tablets 200 g.
3-amino-4-methyl-1-(3-chlorobenzyl)-pyrasol-5-one are comminuted to give a powder, mixed with 300 g lactose and 200 g of potato starch and, after moistening with an aqueous gelatin solution, granulated through a sieve. After drying, 60 g talc and 5 g sodium lauryl sulphate are added and the mixture is compressed to give 10,000 tablets each with a content of active compound of 20 mg.

b. Ampoules of injectable solution for parenteral use 20 g of the sodium salt of 3-amino-4-methyl-1-(4-chlorobenzyl)-pyrazol-5-one are dissolved in 1000 ml propylene glycol and made up to 2000 ml with water. This solution is filled under aceptic conditions into sterile ampoules each with a content of active compound of 20 mg.

The compounds used according to the present invention cause, on oral or parenteral administration, a strong increase of excretion of water and salt and are therefore useful for the treatment of oedematous and hypertonic conditions and for flushing out toxic substances. In addition, the compounds can be used in the case of acute renal insufficiency.

To demonstrate the diuretic and saluretic effect of the compounds used according to the invention, 3,4-dimethyl-1-(α-methyl-3,4-dichlorobenzyl)-pyrazol-5-one, described in Example 6 was administered to dogs. The other compounds show comparable properties.

Diuresis test with dogs a. Method

Female beagles received with the oesophageal sound every 30 minutes 1 mg/kg of a solution which contained 0.4% NaCl and 0.2% KCl. Thereafter the test preparation was applied orally in 0.5 mg/kg 0.1% strength tragacanth mucilage and the change of electrolyte excretion in the urine was measured by comparison with control groups. From the urine volume and the measured electrolyte concentration the excretion could then be calculated in $\mu$ gram-equivalent/kg. Sodium and potassium were determined by flame photometry.

b. Results

The results are shown in Table 1. The renal sodium and water excretion was considerably increased after oral administration of the test preparation. The effect was dependent on the dose.

Table 1

| | | Excretion in $\mu$ g/eq./kg/30 min. ($Na^+ + K^+$) and in ml/kg/30 min. (urine) | | | | | | |
|---|---|---|---|---|---|---|---|---|
| | Min.after appl. | 1–30 | 31–60 | 61–90 | 91–120 | 121–150 | 151–180 | Total excretion after application |
| Control | urine | 1.1 | 1.3 | 1.3 | 1.4 | 1.4 | 0.7 | 7.2 |
| | $Na^+$ | 68 | 79 | 45 | 57 | 51 | 36 | 336 |
| | $K^+$ | 88 | 88 | 64 | 45 | 42 | 25 | 352 |
| 1 mg/kg p.o. | urine | 4.4 | 11.7 | 6.9 | 4.3 | 2.3 | 1.6 | 31.2 |
| | $Na^+$ | 442 | 1341 | 858 | 550 | 269 | 150 | 3610 |
| | $K^+$ | 201 | 245 | 139 | 106 | 82 | 80 | 853 |
| 3 mg/kg p.o. | urine | 6.2 | 10.6 | 8.5 | 7.7 | 4.2 | 3.3 | 40.5 |
| | $Na^+$ | 507 | 1015 | 992 | 914 | 467 | 349 | 4244 |
| | $K^+$ | 143 | 262 | 225 | 210 | 162 | 157 | 1159 |

Effect of 3-methyl-4-methyl-1-(α-methyl-3,4-dichlorobenzyl-pyrazol-5-one on the renal electrdyte and urine excretion in awake dogs in its time course and its total effect after 3 hours. (Mean values of, in each case, 4 animals).
p.s. = per os.

The effect of other compounds representative of those of the present invention is set forth below in Table 2:

Table 2

| | Excretion in μg/eq./kg/h (Na⁺ + K⁺) and in ml/kg/h (urine) | | | |
|---|---|---|---|---|
| | Dose* | Na⁺ | K⁺ | Urine |
| Control | — | 168 | 136 | 2.4 |
| (Example 1) [3,4-dichlorobenzyl pyrazolone structure] | 3 | 637 | 319 | 5.7 |
| (Example 5) [α-methylbenzyl dimethyl pyrazolone structure] | 3 | 1347 | 223 | 11.2 |
| (Example 8) [4-methyl-α-methylbenzyl dimethyl pyrazolone structure] | 3 | 1158 | 358 | 10.5 |
| (Example 9) [phenoxyethyl dimethyl pyrazolone structure] | 3 | 1717 | 229 | 13.5 |
| (Example 39) [phenoxyethyl-4-methyl-5-amino pyrazolone structure] | 3 | 2131 | 339 | 18.5 |

*given orally - expressed as mg/kg. body weight

The following non-limitative examples more particularly illustrate the present invention.

EXAMPLE 1

4-methyl-1-(3,4-dichlorobenzyl)-pyrazol-5-one

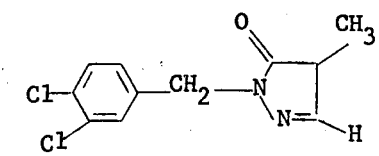

To a solution of 7.5 g of α-formylpropionic acid ethyl ester in 50 ml ethanol were added dropwise 10.9 g 3,4-dichlorobenzylhydrazine. After stirring overnight at room temperature, the solvent was distilled off in a vacuum and the solid residue was recrystallized from ethanol. m.p. 156°C, 9.3 g (64% of theory).

EXAMPLE 2

3,4-dimethyl-1-(β-phenyl-ethyl)-pyrazol-5-one

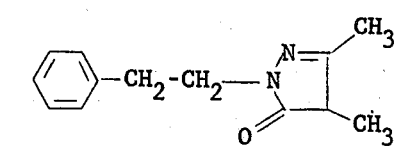

To a solution of 14.4 g (0.1 mole) of α-methylacetoacetic acid ester in 20 ml ethanol were added, under N₂ gas, 13.6 g (0.1 mole) phenylethylhydrazine in ethanol; the temperature rose to 70°C. The reaction mixture, after completion of the addition, was heated under reflux for 2 hours.

When cold, the reaction product crystallized out. It was recrystallized from ethanol.

m.p. 161°C – 163°C Yield 12.6 g (58% of theory)

In a manner analogous to that described in Example 2, the compounds set forth in Table 3 may be similarly obtained.

Table 3

| Example No. | Structural formula | Recrystallization from | Yield (% of theory) | Melting point (°C) |
|---|---|---|---|---|
| 3 | [structure: 4-isopropylbenzyl-dimethylpyrazolone] | ethanol | 70% | 148 – 150 |
| 4 | [structure: 4-methylbenzyl-dimethylpyrazolone] | acetonitrile | 65% | 174 – 176 |
| 5 | [structure: 1-phenylpropyl-dimethylpyrazolone] | ethanol | 82% | 158 – 160 |
| 6 | [structure: 3,4-dichloro-α-methylbenzyl-dimethylpyrazolone] | ethanol | 60% | 160 – 162 |
| 7 | [structure: 1-phenylbutyl-dimethylpyrazolone] | methanol | 59% | 146 – 148 |
| 8 | [structure: 4-methyl-α-methylbenzyl-dimethylpyrazolone] | methanol | 50% | 131 – 133 |
| 8a | [structure: 4-fluoro-α-methylbenzyl-dimethylpyrazolone] | ethanol | 43% | 102 – 104 |
| 9 | [structure: phenoxyethyl-dimethylpyrazolone] | ethanol | 85% | 123 – 125 |
| 10 | [structure: phenoxy-methylethyl-dimethylpyrazolone] | methanol | 53% | 137 – 139 |

Table 3-continued

| Example No. | Structural formula | Recrystallization from | Yield (% of theory) | Melting point (°C) |
| --- | --- | --- | --- | --- |
| 11 | ⟨C₆H₅⟩-S-CH₂-CH₂-N\N=C(CH₃)-C(CH₃)=... (pyrazol-5-one, 3,4-dimethyl) | methanol | 85% | 125 – 127 |
| 12 | ⟨C₆H₅⟩-CH(CH₃)-CH₂-N... (3,4-dimethyl-pyrazol-5-one) | methanol/ether | 44% | 115 – 117 |

EXAMPLE 13

3-methyl-4-ethyl-1-(β-phenoxyethyl)-pyrazol-5-one

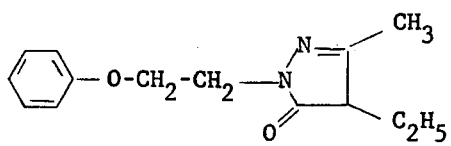

To 15.2 g (0.1 mole) phenoxyethylhydrazine in 20 ml of absolute ethanol were added, under nitrogen, 15.8 g (0.1 mole) α-ethylacetoacetic acid ester. After completion of the exothermic initial reaction, the reaction mixture was heated under reflux for 2 hours. After the mixture had been left to stand overnight, the solvent was drawn off on a rotary evaporator. The residue was dissolved in 2N NaOH. Any unreacted starting products were extracted from the aqueous phase with ether. The aqueous phase was acidified with acetic acid. The reaction product obtained in oily form was taken up in methylene chloride and was obtained herefrom (after drying of the organic phase and evaporation of the solvent) in crystalline form. Recrystallization was effected from methanol.

m.p. 137° - 139°C. Yield 18 g (45% of theory).

In a manner analogous to that described in Example 13, the compounds set forth in Table 4 may be similarly obtained.

Table 4

| Example No. | Structural formula | Recrystallization from | Yield (% of theory) | Melting point (°C) |
| --- | --- | --- | --- | --- |
| 14 | ⟨C₆H₅⟩-CH(CH₃)-N... (3-methyl-4-ethyl-pyrazol-5-one) | ether | 57% | 104 – 106 |
| 15 | Cl,Cl-⟨C₆H₃⟩-CH(CH₃)-N... (3-methyl-4-ethyl-pyrazol-5-one) | ethanol | 55% | 153 – 155 |

EXAMPLE 16

3-allyl-4-methyl-1-(4-chlorobenzyl)-pyrazol-5-one

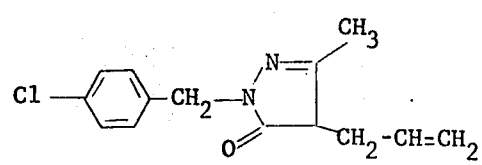

17 g (0.1 mole) allylacetoacetic acid ester were added, under nitrogen, to a mixture of 15.6 g 4-chlorobenzylhydrazine and 30 ml of absolute ethanol; a temperature increase to 55°C took place. The reaction mixture was heated under reflux for 2 hours. When cold, the reaction product crystallized out.

m.p. 146° – 148°C (ethanol) Yield 18.3 g (70% of theory)

In a manner analogous to that described in Example 16, the compounds set forth in Table 5 may be similarly obtained.

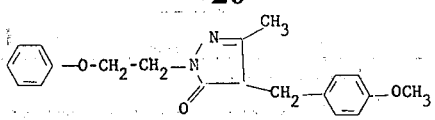

To a solution of 15.2 g phenoxyethylhydrazine in 20 ml of aboslute ethanol were added, in an inert gas atmosphere, 25 g α-(4-methoxybenzyl)-acetoacetic acid ester; the temperature of the reaction mixture in- Table 5

| Example No. | Structural formula | Recrystallization from | Yield (% of theory) | Melting point (°C) |
|---|---|---|---|---|
| 17 | | ethanol | 51.5% | 115 – 117 |
| 18 | | ethanol | 72% | 124 – 125 |
| 19 | | ethanol | 48.5% | 138 – 139 |
| 20 | | petroleum ether/ether | 53% | 70 – 72 |

EXAMPLE 21

3-methyl-4-(4-methoxybenzyl)-1-(β-phenoxyethyl)-pyrazol-5-one creased to 60°C. After 2 hours' heating under reflux and standing overnight, the product crystallized out; it was recrystallized from a mixture of ethanol and a little dimethyl formamide.

m.p. 141° – 142°C Yield 28.5 g (75% of theory)

In a manner analogous to that described in Example 21, the compounds set forth in Table 6 may be similarly obtained.

Table 6

| Example No. | Structural formula | Recrystallization from | Yield (% of theory) | Melting point (°C) |
|---|---|---|---|---|
| 22 | | ethanol | 69% | 142 – 144 |
| 23 | | ethanol | 67% | 146 – 147 |

Table 6-continued

| Example No. | Structural formula | Recrystallization from | Yield (% of theory) | Melting point (°C) |
|---|---|---|---|---|
| 24 | | ethanol | 64% | 172 – 174 |
| 25 | | ethanol | 71% | 137 – 139 |
| 26 | | ethanol/ dimethyl formamide | 78% | 158 – 160 |
| 27 | | dimethyl formamide/ ethanol | 73% | 175 – 177 |

EXAMPLE 28

3-methyl-4-phenyl-1-(β-phenoxyethyl)-pyrazol-5-one

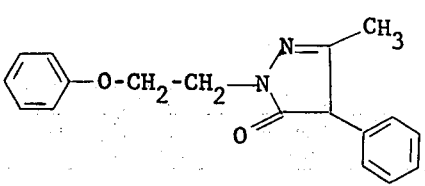

To a solution of 15.2 g (0.1 mole) phenoxyethylhydrazine in 20 ml of absolute ethanol were added dropwise, under nitrogen, 20.6 g α-phenylacetoacetic acid ester; the temperature of the reaction mixture rose to 55°C. After 2 hours' heating of the reaction solution under reflux, the reaction product crystallized during cooling of the reaction mixture. The suction-filtered crystals were washed with ether and recrystallized from methanol.

m.p. 122° – 124°C. Yield 27 g (83% of theory).

In a manner analogous to that described in Example 28, the compounds set forth in Table 7 may be similarly obtained.

Table 7

| Example No. | Structural formula | Recrystallization from | Yield (% of theory) | Melting point (°C) |
|---|---|---|---|---|
| 29 |  | dimethyl formamide/ ethanol | 75% | 227 – 229 |

Table 7-continued

| Example No. | Structural formula | Recrystallization from | Yield (% of theory) | Melting point (°C) |
|---|---|---|---|---|
| 30 | 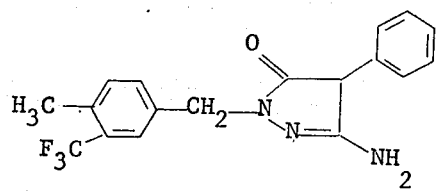 | dimethyl formamide | 79% | 214–216 |

EXAMPLE 31

3-amino-4-phenyl-1-(3-trifluoromethyl-4-methylbenzyl)-pyrazol-5-one

To a solution of 35.3 g α-phenyl-β-amino-β-ethoxyacrylic acid ethyl ester and 1 g p-toluenesulphonic acid in 150 ml ethanol were added dropwise, under nitrogen, 31.5 g 3-trifluoromethyl-4-methylbenzylhydrazine. After stirring overnight, the solvent was distilled off in a vacuum; the residue was recrystallized from dimethyl formamide.

m.p. 211°C. Yield 22 g (42% of theory).

EXAMPLE 32

In a manner analogous to Example 31, 3-amino-4-phenyl-1-(3,4-dichlorobenzyl)-pyrazol-5-one, of the formula:

was prepared.

m.p. 190°C, 40% of theory.

EXAMPLE 33

3-amino-4-n-butyl-1-(3,4-dichlorobenzyl)-pyrazol-5-one

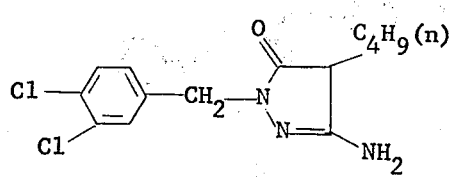

To a solution of 41.1 g α-n-butyl-β-amino-β-ethoxyacrylic acid ethyl ester and a spatula tipfull of p-toluenesulphonic acid in 100 ml ethanol were added dropwise, under nitrogen, 36.5 g 3,4-dichlorobenzylhydrazine. After the mixture had been stirred afterwards for two hours, it was left to stand overnight. The solvent was distilled off, a mixture of ether/petroleum ether (1:1) was added to the residue; the product crystallized through.

m.p. 102°C. Yield 22 g (37% of theory).

In a manner analogous to that described in Example 33, the compounds set forth in Table 8 may be similarly obtained.

Table 8

| Example No. | Structural formula | Recrystallization from | Yield (% of theory) | Melting point (°C) |
|---|---|---|---|---|
| 34 | 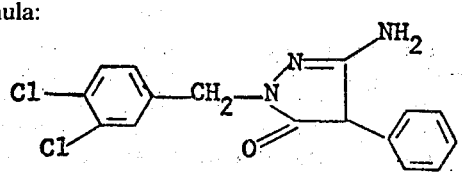 | ethanol | 32% | 109 |
| 35 | | ethanol | 17% | 154 |

EXAMPLE 36

3-amino-4-methyl-4-(4-(4-chlorobenzyl)-pyrazol-5-one

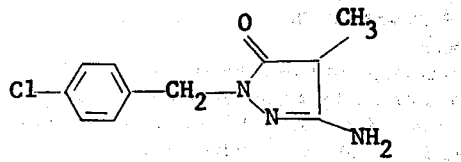

To a solution of 34.6 g β-amino-β-ethoxymethacrylic acid ethyl ester and a spatula tip of p-toluenesulphonic acid in 200 ml ethanol were added dropwise, under nitrogen, 31.2 g p-chlorobenzylhydrazine; the temperature rose from 21°C to 31°C. After standing overnight, the precipitated product was filtered off with suction and recrystallized from ethanol.
m.p. 174°C. Yield 22 g (46% of theory).

In a manner analogous to that described in Example 36, the compounds set forth in Table 9 may be similarly obtained.

antihypertensive amount of a pyrazol-5-one of the formuala:

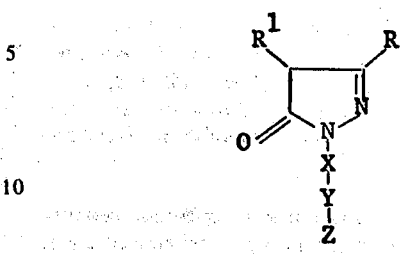

or a pharmaceutically acceptable nontoxic salt thereof wherein

R is hydrogen or lower alkyl;

$R^1$ is lower alkyl, alkenyl of 2 to 4 carbon atoms, phenyl or benzyl unsubstituted or substituted in the phenyl moiety by 1 or 2 of the same or different substituents selected from the group consisting of lower alkyl, lower alkenyl, lower alkoxy, lower alkenoxy, halogen, nitro, cyano and trifluoromethyl;

X is methylene, ethylene, methylene wherein 1 hy-

Table 9

| Example No. | Structural formula | Recrystallization from | Yield (% of theory) | Melting point (°C) |
| --- | --- | --- | --- | --- |
| 37 | Cl-C6H3(Cl)-CH2-N...NH2, CH3 | ethanol | 54% | 147 |
| 38 | Naphthyl-CH2-N...NH2, CH3 | ethanol | 45% | 120 |
| 39 | C6H5-O-CH2-CH2-N...NH2, CH3 | ethanol | 50% | 126 |

What is claimed is:

1. A pharmaceutical composition useful for effecting diuresis and saluresis and for treating hypertension in humans and animals which comprises a diuretically effective amount, a saluretically effective amount or an antihypertensive amount of a pyrazol-5-one of the formuala:

drogen atom is substituted by lower alkyl, or ethylene wherein 1 hydrogen atom on one of the carbon atoms is substituted by lower alkyl or 1 hydrogen atom on each of the two carbon atoms is substituted by lower alkyl;

Y is a direct bond; and

Z is phenyl or naphthyl unsubstituted or nuclear substituted by:
  a. 1 to 3 halogens;
  b. 1 or 2 of the same or different substituents selected from the group consisting of halogen, trifluoromethyl, lower alkyl, lower alkenyl, lower alkoxy, lower alkenoxy, cycloalkyl of 5 to 7 carbon atoms and cycloalkenyl of 5 to 7 carbon atoms;
  c. nitro; or
  d. nitro and 1 or 2 of the same or different substituents selected from the group consisting of lower alkyl, lower alkenyl, lower alkoxy, halogen, and trifluoromethyl;

in combination with a pharmaceutically acceptable nontoxic inert diluent or carrier.

2. A pharmaceutical composition according to claim 1 wherein
  R is hydrogen or alkyl of 1 to 4 carbon atoms;
  R¹ is alkyl of 1 to 4 carbon atoms, alkenyl of 2 to 4 carbon atoms, phenyl, benzyl, or benzyl substituted in the nuclear portion by 1 or 2 of the same or different substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen, nitro, cyano and trifluoromethyl;
  X is methylene, ethylene, methylene wherein 1 hydrogen atom is substituted by alkyl of 1 to 4 carbon atoms or ethylene wherein 1 hydrogen atom is substituted by alkyl of 1 to 4 carbon atoms or 1 hydrogen atom on each of the two carbon atoms is substituted by alkyl of 1 to 4 carbon atoms; and
  Z is phenyl or naphthyl unsubstituted or nuclear substituted by:
    a. 3 halogens;
    b. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, alkenoxy of 2 to 4 carbon atoms, cycloalkyl of 5 to 7 carbon atoms, and cycloalkenyl of 5 to 7 carbon atoms;
    c. trifluoromethyl or nitro; or
    d. nitro, and 1 or 2 of the same or different substituents selected from the group consisting of alkyl of 1 to 4 carbon atoms, alkenyl of 2 to 4 carbon atoms, alkoxy of 1 to 4 carbon atoms, halogen and trifluoromethyl.

3. A pharmaceutical composition according to claim 1 wherein
  R is hydrogen or alkyl of 1 to 4 carbon atoms;
  R¹ is alkyl of 1 to 4 carbon atoms, phenyl, benzyl, or benzyl having 1 or 2 nuclear substituents which are the same or different selected from the group consisting of alkyl of 1 to 4 carbon atoms, alkenyl of 2 to 4 carbon atoms, alkoxy of 1 to 4 carbon atoms, alkenoxy of 2 to 4 carbon atoms, fluorine, chlorine, bromine, nitro, cyano, and trifluoromethyl;
  X is methylene, ethylene, or methylene or ethylene wherein 1 hydrogen atom of each carbon atom is substituted by alkyl of 1 to 4 carbon atoms; and
  Z is phenyl or naphthyl unsubstituted or nuclear substitued by:
    a. 1 or 2 alkyl moieties of 1 to 8 carbon atoms or alkenyl moieties of 2 to 8 carbon atoms;
    b. 1 or 2 alkoxy moieties of 1 to 6 carbon atoms, alkenoxy moieties of 2 to 6 carbon atoms, cycloalkyl moieties of 5, 6 or 7 carbon atoms, or cycloalkenyl moieties of 5, 6 or 7 carbon atoms;
    c. 1, 2 or 3 halogens;
    d. 1 or 2 trifluoromethyl moieties; or
    e. nitro.

4. A pharmaceutical composition according to claim 3 wherein
  Z is phenyl, naphthly, or phenyl substituted by:
    a. 1 or 2 alkyl moieties of 1 to 4 carbon atoms or alkenyl moieties of 2 to 4 carbon atoms;
    b. 1 or 2 alkoxy moieties of 1 to 6 carbon atoms, alkenoxy moieties of 2 to 6 carbon atoms, cycloalkyl moieties of 5 to 7 carbon atoms, or cycloalkenyl moieties of 5 to 7 carbon atoms;
    c. 1, 2 or 3 halogens;
    d. 1 or 2 trifluoromethyl moieties; or
    e. nitro.

5. A pharmaceutical composition according to claim 1 wherein
  R is hydrogen or alkyl of 1 or 2 carbon atoms;
  R¹ is alkyl of 1 or 2 carbon atoms;
  X is methylene, ethylene, methylene wherein 1 hydrogen atom is substituted by alkyl of 1 to 3 carbon atoms, ethylene wherein 1 hydrogen atom on one of the carbon atoms is substituted by methyl, or ethylene wherein 1 hydrogen atom on each of the two carbon atoms is substituted by methyl;
  Y is a direct bond; and
  Z is phenyl, naphthyl, or phenyl substituted by 1 or 2 of the same or different substituents selected from the group consisting of chlorine, bromine, fluorine, iodine, alkyl of 1 to 4 carbon atoms, alkoxy of 1 to 4 carbon atoms, and trifluoromethyl, or by 1 chlorine, bromine, fluorine or iodine and 1 nitro.

6. A pharmaceutical composition according to claim 1 wherein
  R is hydrogen or methyl;
  R¹ is methyl;
  X is methylene, ethylene, methylene wherein 1 hydrogen atom is substituted by methyl or propyl, ethylene wherein 1 hydrogen atom on one of the carbon atoms is substituted by methyl, or ethylene wherein 1 hydrogen atom on each of the two carbon atoms is substituted by methyl;
  Y is a direct bond;
  Z is phenyl, naphthyl, or phenyl substituted by chlorine, bromine, fluorine, iodine, methyl, isopropyl, n-butyl, trifluoromethyl, nitro, cyclohexyl, methoxy, isopropoxy, dichloro, dibromo, chloro and bromo, fluoro and chloro, chloro and methyl, fluoro and trifluoromethyl, or methyl and trifluoromethyl.

7. A pharmaceutical composition according to claim 1 wherein
  R is hydrogen, or alkyl of 1 or 2 carbon atoms;
  R¹ is alkyl of 1 to 4 carbon atoms, allyl, phenyl or benzyl unsubstituted or substituted in the ring by alkoxy of 1 or 2 carbon atoms;
  X is methylene, ethylene, methylene wherein 1 hydrogen atom is substituted by alkyl of 1 to 3 carbon atoms, or ethylene wherein 1 hydrogen atom on one of the carbon atoms is substituted by methyl;
  Y is a direct bond; and
  Z is phenyl, naphthyl, or phenyl substituted by 1 or 2 of the same or different substituents selected from the group consisting of chlorine, fluorine, alkyl of 1 to 4 carbon atoms, and trifluoromethyl.

8. A pharmaceutical composition according to claim 1 wherein
R is hydrogen, or methyl;
R¹ is alkyl of 1 to 4 carbon atoms, allyl, phenyl, benzyl or methoxybenzyl;
X is methylene, ethylene, methylene wherein 1 hydrogen atom is substituted by alkyl of 1 to 3 carbon atoms, or ethylene wherein 1 hydrogen atom on one of the carbon atoms is substituted by methyl;
Y is a direct bond; and
Z is phenyl, naphthyl, or phenyl substituted by fluorine, chlorine, alkyl of 1 to 3 carbon atoms, two chlorines, or methyl and trifluoromethyl.

9. The pharmaceutical composition according to claim 1 wherein the pyrazol-5-one is

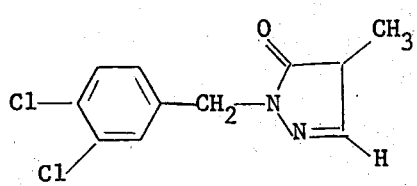

10. The pharmaceutical composition according to claim 1 wherein the pyrazol-5-one is

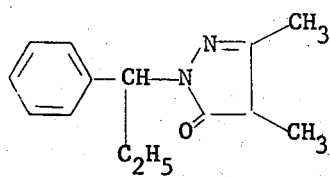

11. The pharmaceutical composition according to claim 1 wherein the pyrazol-5-one is

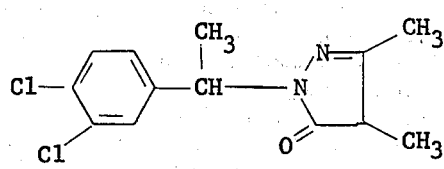

12. The pharmaceutical composition according to claim 1 wherein the pyrazol-5-one is

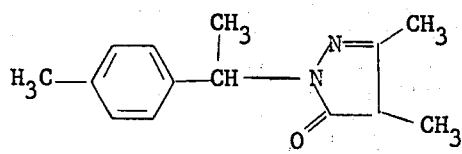

13. A method of effecting diuresis or saluresis and for treating hypertension in humans and animals which comprises administering to such human or animal a diuretically effective amount, a saluretically effective amount or an antihypertensive amount of a pyrazol-5-one of the formula:

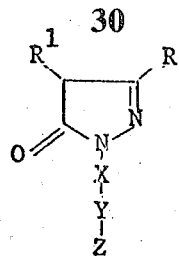

or a pharmaceutically acceptable nontoxic salt thereof wherein
R is hydrogen or lower alkyl;
R¹ is lower alkyl, alkenyl of 2 to 4 carbon atoms, phenyl or benzyl unsubstituted or substituted in the phenyl moiety by 1 or 2 of the same or different substituents selected from the group consisting of lower alkyl, lower alkenyl, lower alkoxy, lower alkenoxy, halogen, nitro, cyano and trifluoromethyl;
X is methylene, ethylene, methylene wherein 1 hydrogen atom is substituted by lower alkyl, or ethylene wherein 1 hydrogen atom on one 9 the carbon atoms is substituted by lower alkyl or 1 hydrogen atom on each of the two carbon atoms is substituted by lower alkyl;
Y is direct bond; and
Z is phenyl or naphthyl unsubstituted or nuclear substituted by:
  a. 1 to 3 halogens;
  b. 1 or 2 of the same or different substituents selected from the group consisting of halogen, trifluoromethyl, lower alkyl, lower alkenyl, lower alkoxy, lower alkenoxy, cycloalkyl of 5 to 7 carbon atoms and cycloalkenyl of 5 to 7 carbon atoms;
  c. nitro; or
  d. nitro and 1 or 2 of the same or different substituents selected from the group consisting of lower alkyl, lower alkenyl, lower alkoxy, halogen, ad trifluoromethyl.

14. A method according to claim 13 wherein
R is hydrogen or alkyl of 1 to 4 carbon atoms;
R¹ is alkyl of 1 to 4 carbon atoms, alkenyl of 2 to 4 carbon atoms, phenyl, benzyl, or benzyl substituted in the nuclear portion by 1 or 2 of the same or different substituents selected from the group consisting of alkyl of 1 to 4 carbon atoms, alkenyl of 2 to 4 carbon atoms, alkoxy of 1 to 4 carbon atoms, alkenoxy of 2 to 4 carbon atoms, halogen, nitro, cyano and trifluoromethyl;
X is methylene, ethylene, methylene wherein 1 hydrogen atom is substituted by alkyl of 1 to 4 carbon atoms, ethylene wherein 1 hydrogen atom on one of the carbon atoms is substituted by alkyl of 1 to 4 carbon atoms or ethylene wherein 1 hydrogen atom on each of the two carbon atoms is substituted by alkyl of 1 to 4 carbon atoms; and
Z is phenyl or naphthyl unsubstituted or nuclear substituted by
  a. 3 halogens;
  b. 1 or 2 of the same or different substituents selected from the group consisting of halogen, trifluoromethyl, alkyl of 1 to 4 carbon atoms, alkenyl of 2 to 4 carbon atoms, alkoxy of 1 to 4 carbon atoms, alkenoxy of 2 to 4 carbon atoms, cycloalkyl of 5 to 7 carbon atoms, and cycloalkenyl of 5 to 7 carbon atoms;
  c. trifluoromethyl or nitro; or
  d. or nitro and 1 to 2 of the same or different substituents selected from the group consisting of alkyl of 1 to 4 carbon atoms, alkenyl of 2 to 4 carbon, atoms, alkoxy of 1 to 4 cabon atoms, halogen and trifluoromethyl.

15. A method according to claim 13 wherein
R is hydrogen;
$R^1$ is alkyl of 1 to 4 carbon atoms, phenyl, benzyl, or benzyl having 1 or 2 or nuclear substituents which are the same or different selected from the group consisting of alkyl of 1 to 4 carbon atoms, alkenyl of 2 to 4 carbon atoms, alkoxy of 1 to 4 carbon atoms, alkenoxy of 2 to 4 carbon atoms, fluorine, chlorine, bromine, nitro, cyano and trifluoromethyl;
X is methylene, ethylene, or methylene wherein 1 hydrogen is substituted by alkyl of 1 to 4 carbon atoms or ethylene wherein 1 hydrogen atom on each of the two carbon atoms is substituted by alkyl of 1 to 4 carbon atoms; and is phenyl or naphthyl unsubstituted or nuclear substituted by:
 a. 1 or 2 alkyl moieties of 1 to 8 carbon atoms or alkenyl moieties of 2 to 8 carbon atoms;
 b. 1 or 2 alkoxy moieties of 1 to 6 carbon atoms, alkenoxy moieties of 2 to 6 carbon atoms, cycloalkyl moieties of 5, 6 or 7 carbon atoms, or cycloalkenyl moieties of 5, 6 or 7 carbon atoms;
 c. 1, 2 or 3 halogens;
 d. 1 or 2 trifluoromethyl moieties; or
 e. nitro.

16. A method according to claim 13 wherein
Z is phenyl, naphthyl, or phenyl substituted by:
 a. 1 or 2 alkyl moieties of 1 to 4 carbon atoms or alkenyl moieties of 2 to 4 carbon atoms;
 b. 1 or 2 alkoxy moieties of 1 to 6 carbon atoms, alkenoxy moieties of 2 to 6 carbon atoms, cycloalkyl moieties of 5 to 7 carbon atoms, or cycloalkenyl moieties of 5 to 7 carbon atoms;
 c. 1, 2 or 3 halogens;
 d. 1 or 2 trifluoromethyl moieties; or
 e. nitro.

17. A method according to claim 13 wherein
R is hydrogen or alkyl of 1 or 2 carbon atoms;
$R^1$ is alkyl of 1 or 2 carbon atoms;
X is methylene, ethylene, methylene wherein 1 hydrogen atom is substituted by alkyl of 1 to 3 carbon atoms, ethylene wherein 1 hydrogen atom on one of the carbon atoms is substituted by methyl, or ethylene wherein 1 hydrogen atom on each of the two carbon atoms is substituted by methyl;
Y is a direct bond; and
Z is phenyl, naphthyl, or phenyl substituted by 1 or 2 of the same or different substituents selected from the group consisting of chlorine, bromine, fluorine, iodine, alkyl of 1 to 4 carbon atoms, alkoxy of 1 to 4 carbon atoms and trifluoromethyl, or by 1 chlorine, bromine, fluorine or iodine and 1 nitro, or by 1 cyclohexyl moiety.

18. A method according to claim 13 wherein
R is hydrogen or methyl;
$R^1$ is methyl;
X is methylene, ethylene, methylene wherein 1 hydrogen atom is substituted by methyl or propyl, etylene wherein 1 hydrogen atom on one of the carbon atoms is substituted by methyl, or ethylene wherein 1 hydrogen atom on each of the two carbon atoms is substituted by methyl moiety;
Y is a direct bond; and
Z is phenyl, naphthyl, or phenyl substituted by chlorine, bromine, fluorine, iodine, methyl, isopropyl, n-butyl, trifluoromethyl, nitro, cyclohexyl, methoxy, isopropoxy, dichloro, dibromo, chloro and bromo, fluoro and chloro, chloro and methyl, fluoro and trifluoromethyl, or methyl and trifluoromethyl.

19. A method according to claim 13 wherein
R is hydrogen, or alkyl of 1 or 2 carbon atoms;
$R^1$ is alkyl of 1 to 4 carbon atoms, allyl, phenyl or benzyl unsubstituted or substituted in the ring by alkoxy of 1 or 2 carbon atoms;
X is methylene, ethylene, methylene wherein 1 hydrogen atom is substituted by alkyl of 1 to 3 carbon atoms, or ethylene wherein 1 hydrogen atom on one of the carbon atoms is substituted by methyl;
Y is a direct bond; and
Z is phenyl, naphthyl, or phenyl substituted by 1 or 2 of the same or different substituents selected from the group consisting of chlorine, fluorine, alkyl of 1 to 4 carbon atoms, and trifluorometyl.

20. A method according to claim 13 wherein
R is hydrogen, or methyl;
$R^1$ is alkyl of 1 to 4 carbon atoms, allyl, phenyl, benzyl or methoxybenzyl;
X is methylene, ethylene, methylene wherein 1 hydrogen atom is substituted by alkyl of 1 to 3 carbon atoms, or ethylene wherein 1 hydrogen atom on one of the carbon atoms is substituted by methyl;
Y is a direct bond; and
Z is phenyl, naphthyl, or phenyl substituted by fluorine, chlorine, alkyl of 1 to 3 carbon atoms, two chlorines, or methyl and trifluoromethyl.

21. The method according to claim 13 wherein the compound is

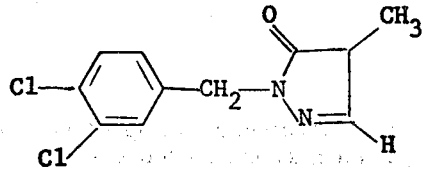

22. The method according to claim 13 wherein the compound is

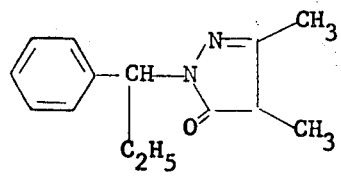

23. The method according to claim 13 wherein the compound is

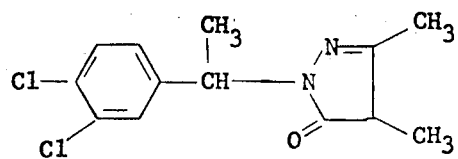

24. The method according to claim 13 wherein the compound is

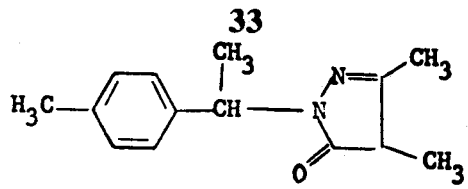
25. A pharmaceutical composition according to claim 1 in oral administration form.
26. A pharmaceutical composition according to claim 1 in parenteral administration form.
27. A pharmaceutical composition according to claim 1 in tablet form.
28. A pharmaceutical composition according to claim 1 in the form of a sterile injectable solution.
* * * * *